(12) United States Patent
Lore et al.

(10) Patent No.: US 10,624,570 B2
(45) Date of Patent: Apr. 21, 2020

(54) USER FATIGUE LEVEL ANALYSIS COMPONENT

(71) Applicant: Essilor International, Charenton-le-Pont (FR)

(72) Inventors: Marie Lore, Charenton-le-Pont (FR); Coralie Barrau, Charenton-le-Pont (FR); Thierry Villette, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 375 days.

(21) Appl. No.: 15/197,108

(22) Filed: Jun. 29, 2016

(65) Prior Publication Data
US 2017/0000399 A1      Jan. 5, 2017

(30) Foreign Application Priority Data

Jul. 1, 2015 (EP) ..................... 15306067

(51) Int. Cl.
*A61B 5/00* (2006.01)
*A61B 5/16* (2006.01)
(Continued)

(52) U.S. Cl.
CPC ............ *A61B 5/165* (2013.01); *A61B 5/1103* (2013.01); *A61B 5/18* (2013.01); *A61B 5/4815* (2013.01);
(Continued)

(58) Field of Classification Search
CPC ..... A61B 5/165; A61B 5/1103; A61B 5/4815; A61B 5/6803; G08B 21/06
See application file for complete search history.

(56) References Cited

U.S. PATENT DOCUMENTS 6,147,612 A    11/2000 Ruan et al.
2006/0079800 A1*  4/2006 Martikka ............. A61B 5/0488
                                                    600/546
(Continued)

FOREIGN PATENT DOCUMENTS

KR    2010 0120633     11/2010
WO    WO 2015/074918 A1   5/2015

OTHER PUBLICATIONS

Search Report dated Sep. 8, 2015, in European Patent Application No. 15 30 6067 (1 pg.).

*Primary Examiner* — Max F Hindenburg
(74) *Attorney, Agent, or Firm* — Oblon, McClelland, Maier & Neustadt, L.L.P.

(57) ABSTRACT

The disclosed embodiments include user fatigue level analysis components, real-time visual behavior measuring devices, and methods for determining the fatigue level of a user. In one embodiment, a user fatigue level analysis component includes a memory configured to store computer executable instructions and a processor for executing the computer executable instructions. The computer executable instructions comprise instructions for receiving at least a visual behavior parameter indicative of the real time visual behavior of the user, for providing at least one sleep quality history parameter indicative of the sleep quality history of the user, and for determining the fatigue level of the user based on the analysis of the combination of the at least one visual behavior parameter and the at least one sleep quality history parameter.

16 Claims, 2 Drawing Sheets

(51) Int. Cl.
   *G08B 21/06*   (2006.01)
   *A61B 5/18*    (2006.01)
   *A61B 5/11*    (2006.01)
   *G08B 31/00*   (2006.01)

(52) U.S. Cl.
   CPC .......... *A61B 5/6803* (2013.01); *A61B 5/7282* (2013.01); *G08B 21/06* (2013.01); *A61B 2560/0242* (2013.01); *G08B 31/00* (2013.01)

(56) References Cited

U.S. PATENT DOCUMENTS

| | | | |
|---|---|---|---|
| 2007/0273611 A1* | 11/2007 | Torch | A61B 3/0066 345/8 |
| 2008/0001735 A1* | 1/2008 | Tran | G06F 19/3418 340/539.22 |
| 2013/0006064 A1* | 1/2013 | Reiner | A61B 5/4884 600/300 |
| 2013/0044291 A1* | 2/2013 | Kato | A61B 3/0025 351/209 |
| 2013/0243208 A1 | 9/2013 | Fawer | |
| 2014/0347366 A1 | 11/2014 | Emori et al. | |
| 2015/0206090 A1* | 7/2015 | Pakhchanyan | G06F 3/04895 705/7.42 |

* cited by examiner

USER FATIGUE LEVEL ANALYSIS COMPONENT

FIELD OF THE INVENTION invention relates to a user fatigue level analysis component, a real-time visual behavior measuring device and a method for determining the fatigue level for a user.

BACKGROUND OF THE INVENTION

Determining the level of fatigue of a user may be useful in many situations. For example, some activities require a great degree of concentration. It is useful to be able to provide to the user carrying out such activity or a third party an indication of the level of fatigue of the user. Indeed, it has been observed that a change in behavior upon carry out an activity may lead to very different results in terms of achievement of the activity. Typically, when a person is driving it can be very useful to analyze the fatigue level of the person so as to provide an alert when the determined fatigue level is greater than a threshold value and driving represents a risk. Therefore, there is a need for a device and a method for determining accurately the fatigue level of a person. One object of the present invention is to provide such a device and method providing such determination.

BRIEF DESCRIPTION OF THE DRAWINGS

Embodiments of the invention will now be described, by way of example only, and with reference to the following drawings in which.

SUMMARY OF THE INVENTION

Figure 1:
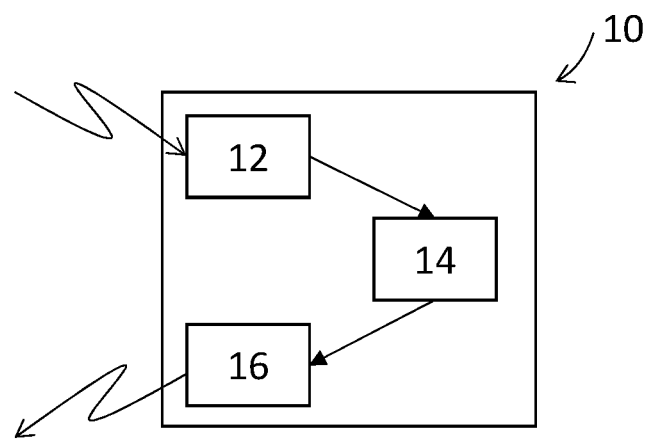
FIG. 1 is a schematic representation of a user fatigue level analysis component according to the invention.

The disclosed embodiments include user fatigue level analysis components, real-time visual behavior measuring devices, and methods for determining the fatigue level of a user. In accordance with some embodiments, the invention proposes a user fatigue level analysis component comprises a memory configured to store computer executable instructions; and a processor for executing the computer executable instructions, wherein the computer executable instructions comprise instructions for receiving at least a visual behavior parameter indicative of the real time visual behavior of the user in activity; providing at least one sleep quality history parameter indicative of the sleep quality history of the user, the sleep quality history being determined when the user is sleeping, for example using objective measurements relating to the user; and determining the fatigue level of the user based on the analysis of the combination of the at least one visual behavior parameter and the at least one sleep quality history parameter.

Advantageously, determining the fatigue level of the user based on the analysis of the combination of the real time visual behavior of the user and the sleep quality history of the user provides a highly accurate estimate of the fatigue level of the user. Indeed, the inventors have observed that the real time visual behavior of a person may be linked very precisely to the fatigue level of the user, however combining the real time visual behavior with the sleep quality history improves the accuracy of the indication of the fatigue level of the user.

According to one or more of the foregoing embodiments of the user fatigue level analysis component, the user fatigue level analysis component comprises at least one of the following. In one of such embodiments, the visual behavior parameter relates at least to the eyelids activity of the user. In another one of such embodiments, the computer executable instructions further comprise instructions for receiving real-time head movement data relating to real time movement of the head of the user, and determining the fatigue level considering the real-time head movement data. In a further one of such embodiments, the computer executable instructions further comprise instructions for receiving real-time environment data relating to at least one real-time parameter of the environment of the user, and determining the fatigue level considering the real-time environment data.

In a further one of such embodiments, the real-time parameter of the environment of the user relates to the features of the light received by the user, said features comprising at least one of the temporal features, the spectral features, the intensity of the light. In a further one of such embodiments, the real-time parameter of the environment of the user relates to temperature and/or the noise of the environment of the user and/or the time of the day. In a further one of such embodiments, the computer executable instructions further comprise instructions for receiving real-time physiological data relating to at least one real-time parameter of the physiology of the user, and determining the fatigue level considering the real-time physiological data. In a further one of such embodiments, the real-time parameter of the physiology of the user relates to sweating of the user and/or the pulse of the user and/or the breathing rhythm of the user and/or muscle spasm of the user.

In a further one of such embodiments, the computer executable instructions further comprise instructions for receiving life habit data relating to at least one parameter of the life habit of the user, and adjusting the fatigue level based on the life habit data. In a further one of such embodiments, the parameter of the life habit of the user relates to the food habits of the user and/or the physical activity habits of the user and/or the rhythm of life of the user. In a further one of such embodiments, the sleep quality history parameter relates at least to the sleep cycles efficiency history of the user. In a further one of such embodiments, the sleep quality history parameter relates at least to sleeping physiological data relating to at least one parameter of the physiology of the user upon sleeping and the computer executable instructions further comprise instructions for determining the fatigue level considering the real-time physiological data. In a further one of such embodiments, the parameter of the physiology of the user upon sleeping relates to breathing of the user upon sleeping and/or the movement of the user upon sleeping and/or to the pulse of the user upon sleeping and/or the sound produced by the user upon sleeping.

In a further one of such embodiments, the sleep quality history parameter relates at least to sleeping environment data relating to at least one parameter of the environment of the user upon sleeping, and the computer executable instructions further comprise instructions for determined the fatigue level considering the sleeping environment data. In a further one of such embodiments, the parameter of the environment of the user upon sleeping relates to the temperature of the sleeping environment of the user and/or the noise of the sleeping environment of the user and/or the features of the light of the sleeping environment of the user received by the user, said the light of the sleeping environment comprise at least one of the temporal features, the spectral features, the intensity of the light. In a further one of such embodiments, the computer executable instructions further comprise instructions for receiving a feedback from the user on his level of fatigue, and adjusting the analyze of the combination of the at least one visual behavior parameter and the at least one sleep quality history parameter used to determine the fatigue, such adjustment being based on the feedback from the user.

In accordance with some embodiments, the invention further relates to a real-time visual behavior measuring device comprising at least one sensor configured to measure in real time at least one visual behavior parameter indicative of the visual behavior of the user and a communication unit configured to communicate the measured real time visual behavior parameter to a user fatigue level analysis component according to the invention.

The invention further relates to an assembly comprising a user fatigue level analysis component according to the invention and a real-time visual behavior measuring device comprising at least one sensor configured to measure in real time at least one visual behavior parameter indicative of the visual behavior of the user and a communication unit configured to communicate the measured real time visual behavior parameter to the user fatigue level analysis component. The real-time visual behavior measuring device may be a head mounted device arranged to be mounted on the head of the user.

In accordance with some embodiments, the invention further relates to a system for determining the fatigue level of a user, the system comprising a real-time visual behavior measuring device according to the invention, a memory storing sleep quality parameter indicative of the sleep quality of the user, and a user fatigue level analysis component according to the invention.

In accordance with some embodiments, the invention further relates to a method for determining the fatigue level for a user, the method comprising a real-time visual behavior measuring step, during which at least one visual behavior parameter indicative of the visual behavior of the user is measured in real time, a sleep quality history parameter providing step, during which at least one sleep quality history parameter indicative of the sleep quality history of the user is provided, and a analyzing step, during which the fatigue level is determined based on the analyze of the combination of the at least one visual behavior parameter and the at least one sleep quality history parameter.

According to one or more of the foregoing embodiments, the method for determining the fatigue level for a user further comprises at least one of the following. In one of such embodiments, the visual behavior parameter relates at least to the eyelids activity of the user. In another one of such embodiments, the method further comprises a real-time head movement data measuring step during which real-time head movement data relating to the movement of the head of the user are measured in real time, and during the analyzing step the fatigue level is determined considering the real-time head movement data. In a further one of such embodiments, the method further comprises a real-time environment data measuring step during which real-time environment data relating to at least one parameter of the environment of the user are measured in real time, and during the analyzing step the fatigue level is determined considering the real-time environment data. In a further one of such embodiments, the parameter of the environment of the user relates to the features of the light received by the user, said features comprising at least one of the temporal features, the spectral features, the intensity of the light. In a further one of such embodiments, the parameter of the environment of the user relates to temperature and/or the noise of the environment of the user and/or the time of the day.

In a further one of such embodiments, the method further comprises a real-time physiological data measuring step during which real-time physiological data relating to at least one parameter of the physiology of the user are measured in real time, and during the analyzing step the fatigue level is determined considering the real-time physiological data. In a further one of such embodiments, the parameter of the physiology of the user relates to sweating of the user and/or the pulse of the user and/or the breathing rhythm of the user and/or muscle spasm of the user. In a further one of such embodiments, the method further comprises a life habit data providing step during which life habit data relating to at least one parameter of the life habit of the user are provided, and during the analyzing step the fatigue level is adjusted based on the life habit data. In a further one of such embodiments, the parameter of the life habit of the user relates to the food habits of the user and/or the physical activity habits of the user and/or the rhythm of life of the user. In a further one of such embodiments, the sleep quality history parameter relates at least to the sleep cycles efficiency history of the user. In a further one of such embodiments, the sleep quality history parameter relates at least to sleeping physiological data relating to at least one parameter of the physiology of the user upon sleeping, and during the analyzing step the fatigue level is determined considering the real-time physiological data.

In a further one of such embodiments, the parameter of the physiology of the user upon sleeping relates to breathing of the user upon sleeping and/or the movement of the user upon sleeping and/or to the pulse of the user upon sleeping and/or the sound produced by the user upon sleeping. In a further one of such embodiments, the sleep quality history parameter relates at least to sleeping environment data relating to at least one parameter of the environment of the user upon sleeping, and during the analyzing step the fatigue level is determined considering the sleeping environment data. In a further one of such embodiments, the parameter of the environment of the user upon sleeping relates to the temperature of the sleeping environment of the user and/or the noise of the sleeping environment of the user and/or the features of the light of the sleeping environment of the user received by the user, said the light of the sleeping environment comprise at least one of the temporal features, the spectral features, the intensity of the light.

In accordance with some embodiments, the invention further relates to a computer program product comprising one or more stored sequences of instructions that are accessible to a processor and which, when executed by the processor, causes the processor to carry out the steps of the method according to the invention. In accordance with some embodiments, the invention further relates to a computer-readable storage medium having a program recorded thereon; where the program makes the computer execute the method of the invention. In accordance with some embodiments, the invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method.

The desired structure for a variety of these systems will appear from the description below. In addition, embodiments of the present invention are not described with reference to any particular programming language. It will be appreciated that a variety of programming languages may be used to implement the teachings of the inventions as described herein.

DETAILED DESCRIPTION OF PREFERRED EMBODIMENTS

Elements in the figures are illustrated for simplicity and clarity and have not necessarily been drawn to scale. For example, the dimensions of some of the elements in the figure may be exaggerated relative to other elements to help improve the understanding of the embodiments of the present invention.

As illustrated on FIG. 1, the invention relates to a user fatigue level analysis component 10. The fatigue level analysis component may comprise a communication module 12, a memory 14, and a processor 16. The communication module 12 may be arranged to receive data. For example the data may be real time visual behavior data indicative of a visual behavior parameter of the user of the fatigue level analysis component.

The real time visual behavior data are typically measured by sensors and sent to the communication module 12. The sensors may be connected by wires to the communication module or the communication may be wireless. The wireless communication can use different communication protocols such a Bluetooth, Zigbee, Wifi or others. The communication module may further receive sleep history data indicative of at least one sleep quality parameter.

The sleep history data may be stored in a distant entity. The distant entity can include different storing objects such as personal digital assistants, audio/video devices, mobile phones, MPEG-1 Audio Layer 3 (MP3) players, personal computers, laptops, tablets, bluetooth headset, watch, wristband, etc.

The communication with the distant entity is usually wireless communication or via the Internet. The distant entity can be Web servers, file servers, media servers, etc. with which the communication module communicate via any of a number of known protocols, such as the hypertext transfer protocol (HTTP).

The memory 14 stores computer executable instructions that are to be executed by the processor 16. The memory 14 may also store sleep history data indicative of at least one sleep quality parameter of the user of the fatigue level analysis component. The processor 16 is configured to execute at least part of the computer executable instructions stored in the memory 14. The computer executable instructions comprise instructions for having the processor carry out a method of the invention.

Figure 2:
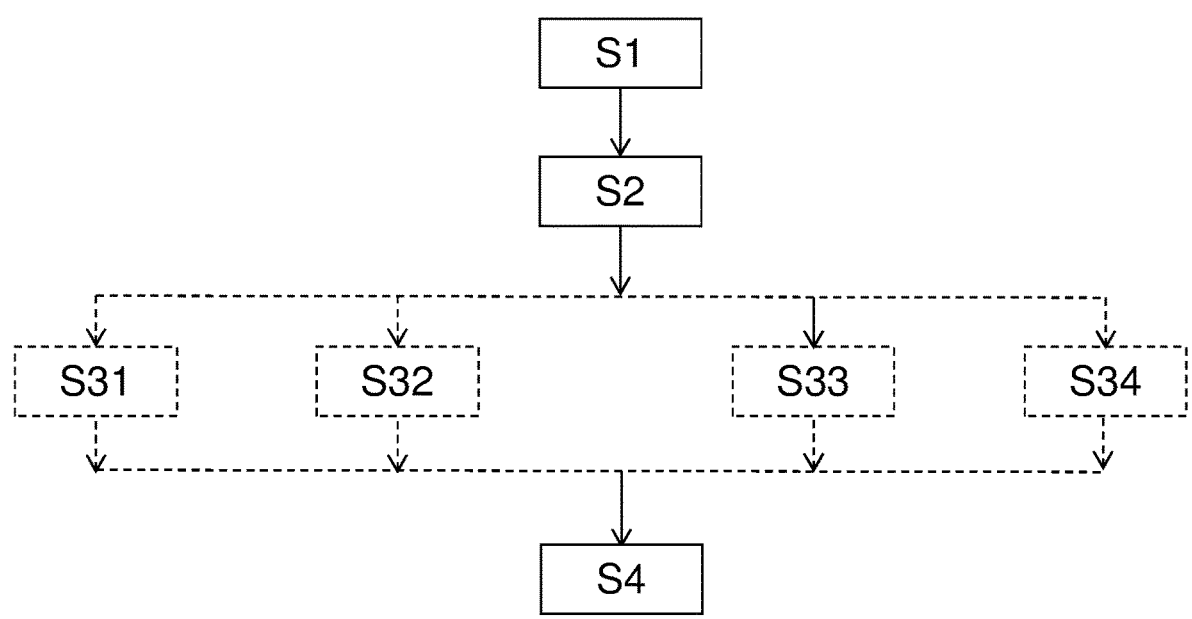
FIG. 2 is an illustration of a chart-flow of a method according to the invention.

As illustrated on FIG. 2, a method of the invention comprises at least a real-time visual behavior receiving step S1, a sleep quality history parameter providing step S2, and an analyzing step S4. During the real-time behavior measuring step S1, at least one visual behavior parameter indicative of the visual behavior of the user is received in real-time. Typically, the visual behavior parameter is measured in real-time by at least one sensor and the measured parameter is sent in real time to the user fatigue level analysis component. For example, the visual behavior parameter may relate at least to the eyelids activity of the user, such as opening frequency and force or shift in the near point of convergence.

In the sense of the invention, "real-time" refers to the fact of measuring and sending the visual behavior parameter of the user at the same time or with a shift smaller than or equal to a few seconds. During the sleep quality history parameter providing step S2, at least one sleep quality history parameter indicative of the sleep quality history of the user is provided to the user fatigue level analysis component.

The sleep quality history parameter may be determined through subjective indication provided by the user. For example, the user may provide each morning an indication on the sleep quality of the night such as a grade depending on the user's feeling of his sleep quality. The sleep quality history may be determined using objective measurements relating to the user when sleeping. For example, the inventors have observed that a sleep quality history parameter relating to the sleep cycles efficiency history of the user is highly relevant when determining the fatigue level of the user.

The sleep quality history parameter may relate at least to sleeping physiological data relating to at least one parameter of the physiology of the user upon sleeping. The sleeping physiological data may for example be obtained by measuring the breathing of the user upon sleeping and/or the movement of the user upon sleeping and/or to the pulse of the user upon sleeping and/or the sound produced by the user upon sleeping.

The environment of the user upon sleeping may influence the sleep quality of the user. Therefore, according to an embodiment of the invention, the sleep quality history parameter relates at least to sleeping environment data relating to at least one parameter of the environment of the user upon sleeping. For example, the parameter of the environment of the user upon sleeping may relates to the temperature of the sleeping environment of the user and/or the noise of the sleeping environment of the user and/or the features of the light of the sleeping environment of the user received by the user, said the light of the sleeping environment comprise at least one of the temporal features, the spectral features, the intensity of the light. To increase the accuracy of the fatigue level determination, the light of the sleeping environment may be combined with the timing in the sleep cycle upon which such light is received by the user.

During the analyzing step S4, the fatigue level is determined based on the analysis of the combination of the visual behavior parameter and the sleep quality history parameter. As indicated previously, combining real-time visual behavior and sleep quality history helps to improve the accuracy and precision of the determination of the fatigue level of the user.

The method of the invention may further comprise a past fatigue level providing step during which data representative of the past fatigue level of the user are provided. During the analyzing step S4 such past fatigue level may be considered to determine more accurately the fatigue level of the user. For example, considering if the user has been having a high level of fatigue recently or not may be used to increase the accuracy of the method of the invention. So as to improve even more the accuracy and precision of the method of the invention, the method may comprise measuring and providing further real time parameters.

As illustrated on FIG. 2, the method of the invention may further comprise at least one of the following steps: a real-time head movement data measuring step S31, and/or a real-time environment data measuring step S32, a real-time physiological data measuring step S33, and a life habit data providing step S34.

During the real-time head movement data measuring step S31, real time head movement data relating to the movement of the head of the user are measured and provided in real-time. During the analyzing step the fatigue level may be determined considering the real-time head movement data. Typically, real-time head movement may be linked to the fatigue level of a user. For example, head tilt or slow decline and sudden rise may provide indication of an increase fatigue level.

The real-time environment of the user may also be considered when determining the fatigue level. During the real-time environment data measuring step S32, real-time environment data relating to at least one parameter of the environment of the user are measured in real time.

During the analyzing step the fatigue level may be determined considering the real-time environment data. For example, the parameter of the environment of the user may relate to the features of the light received in real-time by the user, said features comprising at least one of the temporal features, the spectral features, and the intensity of the light. Further parameters of the environment of the user may be considered as the temperature and/or the noise of the environment of the user and/or the time of the day. Other real time physiological parameters may be related to the fatigue level of the user. During the real-time physiological data measuring step S33, real-time physiological data relating to at least one parameter of the physiology of the user are measured in real time.

During the analyzing step the fatigue level may be determined considering the real-time physiological data. The parameter of the physiology of the user may relate to sweating of the user and/or the pulse of the user and/or breathing rhythm of the user and/or muscle spasm of the user. Life habits of the user may be of interest when determining/predicting the fatigue level of the user. During the life habit data providing step S34 life habit data relating to at least one parameter of the life habit of the user are provided.

During the analyzing step S4, the fatigue level is adjusted based on the life habit data. Typically, the life habit of the user relates to the food habits of the user and/or the physical activity habits of the user and/or the rhythm of life of the user or any other life habit parameter that may have an influence on the fatigue level of the user.

The method of the invention may further comprise a feedback step during which the user provides feedback concerning his current level of fatigue, for example using a scale of fatigue level. The analysis of the combination of the at least one visual behavior parameter and the at least one sleep quality history parameter used to determine the fatigue level may be adjusted based on the feedback from the user. Advantageously, such feedback makes it possible for a user to customize the analysis and therefore helps improve the accuracy of the method of the invention and/or the fatigue level analysis component.

Figure 3:
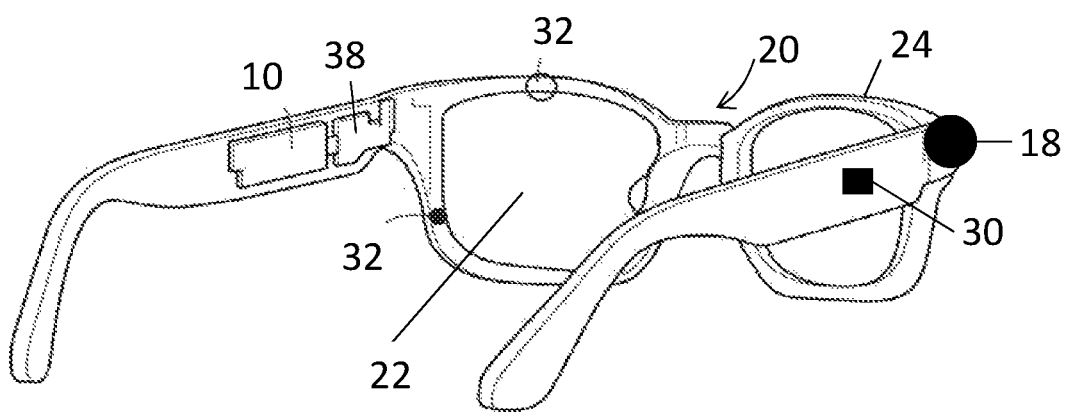
FIG. 3 is a representation of a real time behavior measuring device according to the invention.

As represented on FIG. 3, the invention further relates to real-time visual behavior measuring device 20. The real time visual behavior measuring device comprises at least one sensor 32 configured to measure in real time at least one visual behavior parameter indicative of the visual behavior of the user and a communication unit 38 configured to communicate the measured real time visual behavior parameter to a user fatigue level analysis component 10 according to the invention.

In the example represented on FIG. 3, the real-time visual behavior measuring device 20 is a head mounted device comprising a frame intended to be mounted on the head of the user. Furthermore, in the example of FIG. 3, the user fatigue level analysis component 10 is embedded in the real-time visual behavior measuring device 20.

The invention is not limited to such embodiment; in particular the user fatigue level analysis component 10 could be in a distant entity communicating with the real time visual behavior measuring device with the communication unit. The distant entity can include different computing objects such as personal digital assistants, audio/video devices, mobile phones, MPEG-1 Audio Layer 3 (MP3) players, personal computers, laptops, tablets, Bluetooth headset, watch, wristband, etc. The communication can be done through different communication devices and protocols, like Bluetooth, Zigbee, WiFi or others.

The real-time visual behavior measuring device 20 may comprise different type of sensors depending on the type of real-time parameters that are to be considered. Typically, the real-time visual behavior measuring device 20 may comprise a head movement detection sensor 30 that may comprise an accelerometer and/or gyroscope and/or compass configured to sense the orientation and position and variation of orientation and position of the head of the user. The head movement detection component 30 may be placed on the frame 24 of the real-time visual behavior measuring device 20, as illustrated on FIG. 3.

The real-time visual behavior measuring device may further comprise an eye behavior sensor 32, such as an eye tracking device 32 arranged to measure eye movements and activity of the user. The real-time behavior measuring device may further comprise a light sensor 18 arranged to measure features of light, such as temporal, spectral and intensity features.

The head mounted device 20 represented on FIG. 3 may also comprise two optical lenses 22. The optical lenses 22 may correspond to the optical prescription of the user. The optical lenses 22 may also be active lenses with an optical function which can be adapted for example to the user's needs.

The invention has been described above with the aid of embodiments without limitation of the general inventive concept. Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A user fatigue level analysis component, comprising:
   memory configured to store computer executable instructions; and
   a processor for executing the computer executable instructions, wherein the computer executable instructions comprise instructions for:
   receiving at least one visual behavior parameter indicative of a real time visual behavior of a user in activity;
   receiving real-time head movement data relating to real time movement of the head of the user;
   receiving life habit data relating to at least one parameter of a life habit of the user, the life habit of the user including at least one of: food consumption habits of the user or physical activity habits of the user;
   obtaining at least one sleep quality history parameter indicative of a sleep quality history of the user, the sleep quality history being determined when the user is sleeping;
   determining a fatigue level of the user based on an analysis of a combination of the at least one visual behavior parameter, the at least one sleep quality history parameter and the real-time head movement data; and
   adjusting the fatigue level based on the life habit data.

2. The component of claim 1, wherein a visual behavior parameter of the at least one visual behavior parameter relates at least to an eyelids activity of the user.

3. The component of claim 1, wherein the computer executable instructions further comprise instructions for:
   receiving real-time environment data relating to at least one real-time parameter of an environment of the user; and
   determining the fatigue level considering the real-time environment data.

4. The component of claim 3, wherein a real-time parameter of the at least one real time parameter of the environment of the user relates to features of light received by the user, said features comprising at least one of temporal features, spectral features, intensity of the light.

5. The component of claim 3, wherein a real-time parameter of the at least one real-time parameter of the environment of the user relates to at least one of temperature of the environment of the user, noise of the environment of the user and a time of a day.

6. The component of claim 3, wherein the computer executable instructions further comprise instructions for:
   receiving real-time physiological data relating to at least one real-time parameter of a physiology of the user; and
   determining the fatigue level considering the real-time physiological data.

7. The component of claim 6, wherein a sleep quality history parameter of the at least one sleep quality history parameters relates at least to a sleep cycle efficiency history of the user.

8. The component of claim 7, wherein the sleep quality history parameter relates at least to sleeping physiological data relating to at least one parameter of a physiology of the user upon sleeping, and wherein the computer executable instructions further comprises instructions for determining the fatigue level considering the real-time physiological data.

9. The component of claim 7, wherein the sleep quality history parameter relates at least to sleeping environment data relating to at least one parameter of an environment of the user upon sleeping, and wherein the computer executable instructions further comprise instructions for determining the fatigue level considering the sleeping environment data.

10. The component of claim 1, wherein the computer executable instructions further comprise instructions for:
    receiving a feedback from the user on his level of fatigue; and
    adjusting the analysis of the combination of the at least one visual behavior parameter and the at least one sleep quality history parameter used to determine the fatigue, such adjustment being based on the feedback from the user.

11. A real-time visual behavior measuring device comprising:
    at least one sensor configured to measure in real time at least one visual behavior parameter indicative of the visual behavior of a user; and
    a communication circuit configured to communicate a measured real time visual behavior parameter to a user fatigue level analysis component, the user fatigue level analysis component comprising:
       memory configured to store computer executable instructions; and
       a processor for executing the computer executable instructions,
    wherein the computer executable instructions comprise instructions for:
    receiving at least a visual behavior parameter indicative of the real time visual behavior of the user in activity;
    receiving real-time head movement data relating to real time movement of the head of the user;
    receiving life habit data relating to at least one parameter of a life habit of the user, the life habit of the user including at least one of: food consumption habits of the user or physical activity habits of the user;
    obtaining at least one sleep quality history parameter indicative of the sleep quality history of the user, the sleep quality history being determined when the user is sleeping;
    determining the fatigue level of the user based on the analysis of the combination of the at least one visual behavior parameter, the at least one sleep quality history parameter and the real-time head movement data; and
    adjusting the fatigue level based on the life habit data.

12. The real-time visual behavior measuring device of claim 11, wherein the real-time visual behavior measuring device is a head mounted device arranged to be mounted on the head of the user.

13. A system for determining a fatigue level of a user, the system comprising:
  memory storing sleep quality parameters indicative of a sleep quality of the user,
  a user fatigue level analysis component comprising:
    memory configured to store computer executable instructions; and
    a processor for executing the computer executable instructions,
    wherein the computer executable instructions comprise instructions for:
    receiving at least a visual behavior parameter indicative of a real time visual behavior of the user in activity;
    receiving real-time head movement data relating to real time movement of the head of the user;
    receiving life habit data relating to at least one parameter of a life habit of the user, the life habit of the user including at least one of: food consumption habits of the user or physical activity habits of the user;
    obtaining at least one sleep quality history parameter indicative of the sleep quality history of the user, the sleep quality history
    being determined when the user is sleeping;
    determining the fatigue level of the user based on the analysis of the combination of the at least one visual behavior parameter, the at least one sleep quality history parameter and the real-time head movement data; and
    adjusting the fatigue level based on the life habit data; and
  a real-time visual behavior measuring device comprising:
    at least one sensor configured to measure in real time at least one visual behavior parameter indicative of the visual behavior of the user; and
    a communication circuit configured to communicate a measured real time visual behavior parameter to the user fatigue level analysis component.

14. The system of claim 13, wherein the computer executable instructions further comprise instructions for:
  receiving real-time environment data relating to at least one real-time parameter of an environment of the user; and
  determining the fatigue level considering the real-time environment data.

15. The system of claim 14, wherein the computer executable instructions further comprise instructions for:
  receiving real-time physiological data relating to at least one real-time parameter of a physiology of the user; and
  determining the fatigue level considering the real-time physiological data.

16. The system of claim 13, wherein the computer executable instructions further comprise instructions for:
  receiving a feedback from the user on his level of fatigue; and
  adjusting the analysis of the combination of the at least one visual behavior parameter and the at least one sleep quality history parameter used to determine the fatigue, such adjustment being based on the feedback from the user.

* * * * *